US00PP21813P2

(12) United States Plant Patent
Sakazaki

(10) Patent No.: US PP21,813 P2
(45) Date of Patent: Mar. 22, 2011

(54) *LOBELIA* PLANT NAMED 'USLOB13'

(50) Latin Name: *Lobelia hybrida*
Varietal Denomination: USLOB13

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,762

(22) Filed: Dec. 16, 2009

(51) Int. Cl.
*A01H 5/00* (2006.01)

(52) U.S. Cl. ..... Plt./451

(58) Field of Classification Search ..... Plt./451
See application file for complete search history.

*Primary Examiner*—June Hwu
(74) *Attorney, Agent, or Firm*—C. A. Whealy

(57) ABSTRACT

A new and distinct cultivar of *Lobelia* plant named 'USLOB13', characterized by its upright to outwardly spreading, semi-mounding plant habit; vigorous growth habit; freely branching habit; continuously and freely flowering habit; violet-colored flowers; and relatively high temperature tolerant.

1 Drawing Sheet

Botanical designation: *Lobelia hybrida.*
Cultivar denomination: 'USLOB13'.

BACKGROUND OF THE INVENTION

The present invention relates to a new and distinct cultivar of *Lobelia* plant, botanically known as *Lobelia hybrida* and hereinafter referred to by the name 'USLOB13'.

The new *Lobelia* plant is a product of a planned breeding program conducted by the Inventor in Higashiomi, Shiga, Japan. The objective of the breeding program is to create new uniform *Lobelia* cultivars with good vigor, attractive flower coloration and tolerance to high temperatures.

The new *Lobelia* plant originated from a cross-pollination made by the Inventor on Jun. 17, 2006 of *Lobelia hybrida* 'Hot White', not patented, as the female, or seed, parent with a proprietary seedling selection of *Lobelia hybrida* identified as code number 06LOBJ-03, not patented, as the male, or pollen, parent. The new *Lobelia* plant was discovered and selected by the Inventor as a single flowering plant with the progeny of the stated cross-pollination grown in a controlled greenhouse environment in Higashiomi, Shiga, Japan on May 15, 2007.

Asexual reproduction of the *Lobelia* plant by vegetative cuttings in Higashiomi, Shiga, Japan since May 16, 2007, has shown that the unique features of this new *Lobelia* plant are stable and reproduced true to type in successive generations.

SUMMARY OF THE INVENTION

Plants of the new *Lobelia* have not been observed under all possible environmental conditions. The phenotype may vary somewhat with variations in environment such as temperature and light intensity without, however, any variance in genotype.

The following traits have been repeatedly observed and are determined to be the unique characteristics of 'USLOB13'. These characteristics in combination distinguish 'USLOB13' as a new and distinct cultivar of *Lobelia:*

1. Upright to outwardly spreading, semi-mounding plant habit.
2. Vigorous growth habit.

3. Freely branching habit.
4. Continuously and freely flowering habit.
5. Violet-colored flowers.
6. Relatively high temperature tolerant.

Plants of the new *Lobelia* differ from plants of the female parent, 'Hot White', in the following characteristics:

1. Plants of the new *Lobelia* are more compact than and not as open as plants of 'Hot White'.
2. Plants of the new *Lobelia* and 'Hot White' differ in flower color as plants of 'Hot White' have white-colored flowers.

Plants of the new *Lobelia* differ from plants of the male parent selection primarily in flowers color as plants of the male parent selection have blue-colored flowers.

Plants of the new *Lobelia* can be compared to plants of *Lobelia* 'Regatta Lilac', not patented. In side-by-side comparisons conducted in Bonsall, Calif., plants of the new *Lobelia* differed from plants of 'Regatta Lilac' in the following characteristics:

1. Plants of the new *Lobelia* were more mounding than and not as open as plants of 'Regatta Lilac'.
2. Plants of the new *Lobelia* and 'Regatta Lilac' differed in flower color as plants of 'Regatta Lilac' had lilac-colored flowers.
3. Plants of the new *Lobelia* were more high temperature-tolerant than plants of 'Regatta Lilac'.

Plants of the new *Lobelia* can also be compared to plants of *Lobelia* 'Riviera Lilac', not patented. In side-by-side comparisons conducted in Bonsall, Calif., plants of the new *Lobelia* differed from plants of 'Riviera Lilac' in the following characteristics:

1. Plants of the new *Lobelia* were more mounding than and not as compact as plants of 'Riviera Lilac'.
2. Plants of the new *Lobelia* were more freely branching than plants of 'Riviera Lilac'.
3. Plants of the new *Lobelia* were more high temperature-tolerant than plants of 'Riviera Lilac'.

BRIEF DESCRIPTION OF THE PHOTOGRAPHS

The accompanying colored photographs illustrate the overall appearance of the new *Lobelia* plant, showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the bottom of the sheet comprises a side perspective view of a typical flowering plant of 'USLOB13' grown in a container.

The photograph at the top of the sheet is a close-up view of typical flowers and leaves of 'USLOB13'.

DETAILED BOTANICAL DESCRIPTION

Plants used for the aforementioned photographs and following description were grown under conditions which closely approximate commercial production conditions during the autumn in 10-cm containers in a polyethylene-covered greenhouse in Bonsall, Calif. During the production of the plants, day temperatures ranged from 18° C. to 38° C., night temperatures average 18° C. and light levels ranged from 7,000 to 10,000 foot-candles. Plants were two months old when the photographs and description were taken. In the following description, color references are made to The Royal Horticultural Society Colour Chart, 2007 Edition, except where general terms of ordinary dictionary significance are used.

Botanical classification: *Lobelia hybrida* 'USLOB13'.

Parentage:

*Female parent.*—*Lobelia hybrida* 'Hot White', not patented.

*Male parent.*—Proprietary seedling selection of *Lobelia hybrida* identified as code number 06LOBJ-03, not patented.

Propagation:

*Type cutting.*—Vegetative tip cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 22 days at temperatures ranging from 17° C. to 29° C.

*Time to produce a rooted plant, winter.*—About 25 days at temperatures ranging from 17° C. to 21° C.

*Root description.*—Medium in thickness, fibrous; white in color.

*Rooting habit.*—Moderate branching; medium in density.

Plant description:

*Form.*—Upright to outwardly spreading, semi-mounding plant habit; freely branching habit with about 16 lateral branches per plant each primary lateral developing multiple secondary laterals; vigorous growth habit.

*Plant height.*—About 18 cm.

*Plant width.*—About 36 cm.

*Lateral branch description.*—Length: About 21 cm. Diameter: About 3 mm. Internode length: About 1.6 cm. Strength: Strong, flexible. Texture: Pubescent. Color: Close to 146A.

Foliage description:

*Arrangement.*—Alternate, simple; sessile.

*Length, basal leaves.*—About 4.5 cm.

*Width, basal leaves.*—About 1.4 cm.

*Length, apical leaves.*—About 3 cm.

*Width, apical leaves.*—About 5 mm.

*Shape.*—Elliptical to oblanceolate.

*Apex.*—Acute; recurved.

*Base.*—Attenuate.

*Margin.*—Entire or with shallow and irregular serrations.

*Texture, upper and lower surfaces.*—Pubescent.

*Venation pattern.*—Pinnate; arcuate.

*Color.*—Developing leaves, upper surface: Close to 146A. Developing leaves, lower surface: Close to 146B. Fully expanded leaves, upper surface: Close to 137B; venation, close to 137C. Fully expanded leaves, lower surface: Close to 146B; venation, close to 146B.

Flower description:

*Flower arrangement, form and habit.*—Solitary axillary flowers with three broad lower (two laterals and one lip) petals and two narrower upper (banner) petals, petals fused towards the base into a narrow tube; freely flowering habit with about 14 to 16 flowers and flower buds per lateral stem at one time; flowers face upright to outwardly.

*Natural flowering season.*—Under greenhouse conditions, plants begin flowering about six weeks after planting. Under outdoor conditions, plants begin flowering during the spring and flower continuously until frost in California; flowering indeterminate with new flowers overgrowing older flowers and leaves.

*Flower longevity on the plant.*—Longevity of individual flowers is highly dependent on environmental conditions; flowers typically last about four to five days on the plant; flowers persistent.

*Fragrance.*—None detected.

*Flower buds.*—Length: About 1 cm. Diameter: About 3.5 mm. Shape: Obovate. Color: Close to 145C.

*Flower size.*—About 1.3 cm by 1.6 cm.

*Flower depth (height).*—About 1.9 cm.

*Flower throat diameter.*—About 2 mm by 3 mm.

*Flower tube length.*—About 1 cm.

*Flower tube diameter at base.*—About 1.5 mm.

*Petals.*—Arrangement: Single whorl of five petals, petals fused at the base into a narrow tube; three broad lower (two laterals and one lip) petals and two narrower upper (banner) petals. Three lower petals: Lobe length: About 8 mm. Lobe width: About 5 mm. Shape: Obovate. Apex: Rounded. Margin: Entire. Texture, upper and lower surfaces: Smooth, glabrous; velvety. Two upper petals: Lobe length: About 6 mm. Lobe width: About 2 mm. Shape: Lanceolate. Apex: Rounded. Margin: Entire. Texture, upper and lower surfaces: Smooth, glabrous; velvety. Color, all petals: When opening, upper surface: Close to 85B. When opening, lower surface: Close to 84D. Fully opened, upper surface: Close to N87C; towards the base, close to NN155D; central spots, close to N87A; color becoming closer to 85A with development. Fully opened, lower surface: Close to 85D; towards the apex, close to 85C; color becoming closer to 84D with development. Throat: Close to 84D; tiny flecks, close to 84C. Tube: Close to 84D.

*Sepals.*—Arrangement: Single whorl of five sepals, fused at the base; star-shaped calyx. Length: About 7 mm. Width: About 1 mm. Shape: Lanceolate. Apex: Acute. Margin: Entire. Texture, upper and lower surfaces: Pubescent. Color, upper and lower surfaces: Close to 146A.

*Peduncles.*—Length: About 2.2 cm. Diameter: About 1 mm. Aspect: About 45° from the lateral stem axis. Strength: Moderately strong, flexible. Texture: Pubescent. Color: Close to 146A.

*Reproductive organs.*—Stamens: Quantity per flower: About five. Filament length: About 6 mm. Filament color: Close to 84B to 84D. Anther length: About 2 mm. Anther shape: Lanceolate. Anther color: Close to N77C. Pollen amount: Scarce. Pollen color: Close to 155D. Pistils: Quantity per flower: One. Pistil length: About 1 cm. Stigma shape: Round. Stigma color: Close to 92B. Style length: About 7 mm. Style color: Close to 144C. Ovary color: Close to 144A.

*Seeds/fruits.*—Seed and fruit development have not been observed.

Disease/pest resistance: Plants of the new *Lobelia* have not been noted to be resistant to pathogens and pests common to *Lobelia*.

Temperature tolerance: Plants of the new *Lobelia* have been observed to tolerate temperatures from about 1° C. to about 40° C.; relatively high temperature tolerant.

It is claimed:

1. A new and distinct *Lobelia* plant named 'USLOB13' as illustrated and described.

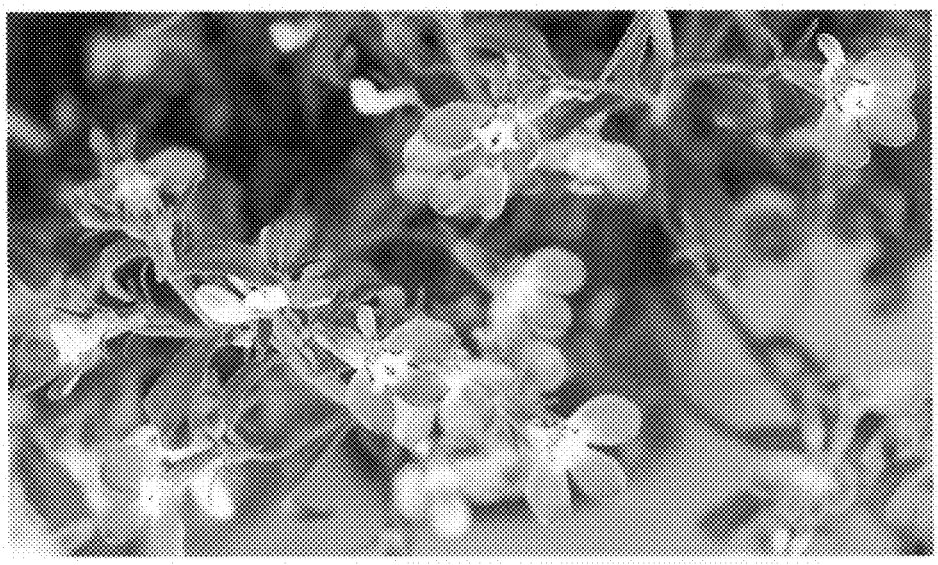
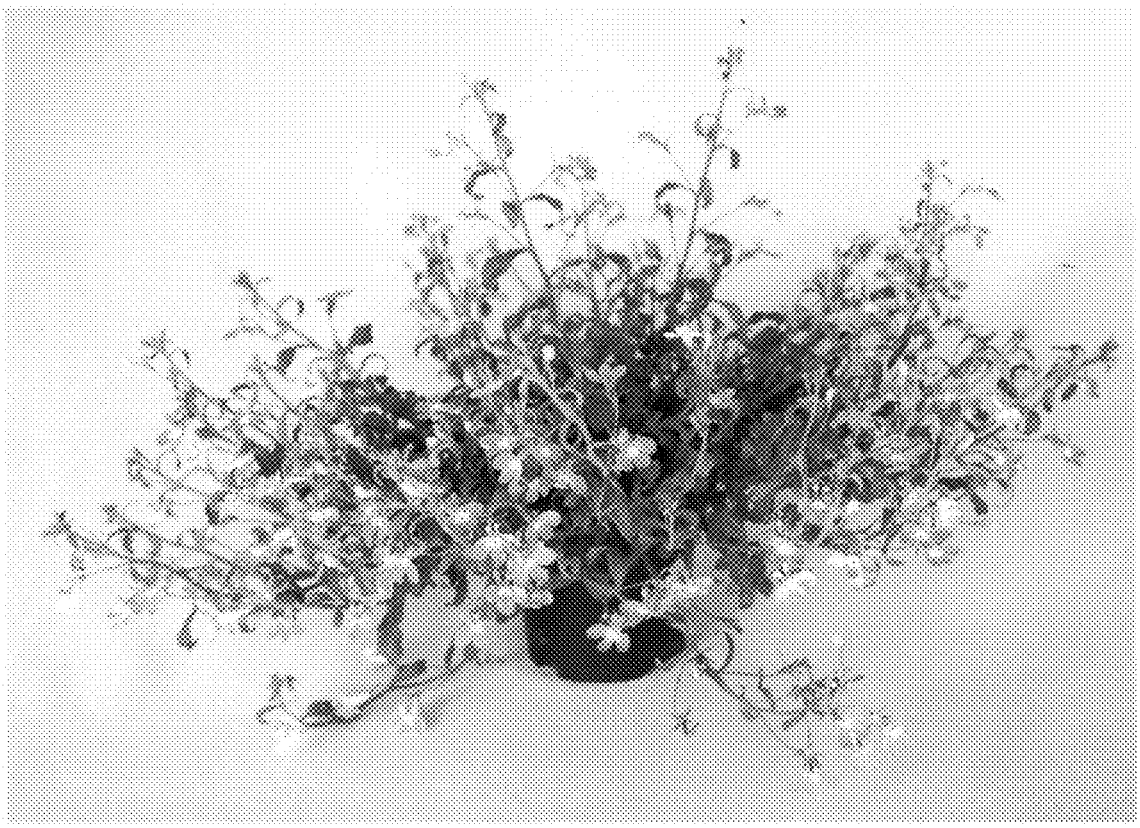

* * * * *